United States Patent [19]

Reid

[11] Patent Number: 5,078,147
[45] Date of Patent: Jan. 7, 1992

[54] METHOD OF NONINVASIVE ULTRASONIC DETECTION OF NERVE ROOT INFLAMMATION

[75] Inventor: John D. Reid, Dodge Center, Minn.

[73] Assignee: Vivo Corporation, Minn.

[21] Appl. No.: 470,113

[22] Filed: Jan. 25, 1990

[51] Int. Cl.$^5$ .............................................. A61B 8/00
[52] U.S. Cl. ............................................... 128/661.01
[58] Field of Search ......... 128/660.01, 660.07–661.01;
73/618–620, 625–626

[56] References Cited
U.S. PATENT DOCUMENTS

| | | | |
|---|---|---|---|
| 4,167,180 | 9/1979 | Kossoff | 128/660.09 |
| 4,476,873 | 10/1984 | Sorenson et al. | 128/661.01 |
| 4,545,385 | 10/1985 | Pirschel | 128/660.09 |
| 4,669,482 | 6/1987 | Ophir | 738/597 |
| 4,694,700 | 9/1987 | Maerfeld | 128/661.01 X |
| 4,785,817 | 11/1988 | Stouffer | 128/660.07 |

FOREIGN PATENT DOCUMENTS

2061504 5/1981 United Kingdom ........... 128/660.07

Primary Examiner—Francis Jaworski
Attorney, Agent, or Firm—John L. Rooney

[57] ABSTRACT

A method of detecting inflammation of a nerve root adjacent to a spine of a patient using an ultrasound apparatus. The present method includes the steps of providing an ultrasound apparatus including an ultrasonic transducer interconnected with a source of electrical energy and with a receiver having amplification means, positioning the ultrasonic transducer on the patient's back in a location lateral to the spine, angling the ultrasonic transducer such that ultrasonic energy can be directed medialad to the spine, transmitting ultrasonic energy toward the nerve root at a power level and a frequency effective to create a reflection from an inflamed nerve root that is detectable by the ultrasound apparatus, and processing ultrasonic energy reflected from the nerve root. Ultrasound apparatus including ultrasonic transducers are also disclosed.

25 Claims, 10 Drawing Sheets

METHOD OF NONINVASIVE ULTRASONIC DETECTION OF NERVE ROOT INFLAMMATION

BACKGROUND OF THE INVENTION

1. Field of the Invention

The present invention generally relates to ultrasonic imaging techniques, specifically medical diagnostic imaging techniques. In particular, the present invention relates to methods of ultrasonic detection of inflamed nerve roots and ultrasound apparatus used therefore.

2. Description of the Prior Art

Medical science has found it useful to sense the internal anatomy of the human body for various purposes such as detection of illness, observation of broken bones, monitoring of fetal viability, inspection of heart valve motion, and tumor detection.

External palpation is commonly used for locating and detecting easily sensed problems such as tumors, swollen organs, and ruptures. While external palpations are useful, they cannot be used to sense fine detail or to detect problems deep within the human body or those covered by other anatomical structures.

In the last 100 years or so, medical science has developed numerous other techniques of examining the internal structure of the body. Some techniques, such as nuclear particles methods and X-ray imaging including the CAT scan, tend to be expensive and require highly trained personnel. Additionally, these methods entail use of ionizing radiation which can damage human tissue.

Ultrasonic techniques have also been developed. These ultrasonic techniques are generally considered safe, can be implemented at low-cost, and can be designed to be easily used by personnel with little training. Examples of ultrasonic techniques include those described in U.S. Pat. No. 4,478,084 which describes an apparatus for ultrasound tomography and U.S Pat. No. 4,167,180 which describes a method and apparatus for performing an ultrasonic examination. However, the use of ultrasound as a diagnostic to study the spine is believed to be underdeveloped.

Some work has been done in ultrasonic spine scanning. Raghavendra and Epstein ("Sonography of the Spine and Spinal Cord," *Radiologic Clinics of North America*, Vol. 23, No. 1, March 1985 pp. 91-105) reported ultrasonic scanning of the spinal cord in young infants and those with spine defects such as spina bifida. However, no indication of detecting the spinal nerve root was given for persons with intact and developed spines. Also, Knake et al ("Neurosurgical Applications of Intraoperative Ultrasound," *Radiologic Clinics of North America*, Vol. 23, No. 1, March 1985 pp. 73-90) reported intraoperative techniques for ultrasonically scanning the spinal cord. However, no discussion of performing a similar function noninvasively was made.

Although the present inventor is unaware of any reported use of noninvasive ultrasound techniques to detect inflammation of nerve roots, it is believed that the ability to detect nerve root inflammation with ultrasound techniques would be a great advance over present method of palpation and heat detection. It will be appreciated that noninvasive ultrasonic detection of nerve root inflammation would be a great aid to health professionals in respect to detecting inflamed nerve roots so that the causes of the inflammation can be addressed before further injury.

One requirement of all ultrasonic imaging is a transducer to generate and detect the ultrasound waves. Because of simplicity of design, either a piezoelectric or an electromagnetic transducer is normally used. Examples of these transducers are the electromagnetic transducer described in U.S. Pat. No. 4,821,245 and the piezoelectric transducer probe described in U.S. Pat. No. 4,582,066.

As previously mentioned, one benefit of ultrasonic imaging is that it can be performed by personnel who do not necessarily have extensive training. This is especially true of machines designed for specific applications because the number of controls required to use the machine are often minimized. If the ultrasonic machine is not designed to suit a particular function, the large number of variables, including (1) velocity of sound wave propagation, (2) power input, (3) sound wave attenuation, (4) reflectiveness of various anatomical features, (5) wavelength, (6) receiver gain and (7) characteristics of the body being scanned, would require that the machine have so many controls that only highly trained technicians could use it.

It would, therefore, be useful and desirable to have both a noninvasive method of ultrasonically detecting inflamed nerve roots and ultrasound apparatus designed for use in accordance with such a method. It would be even more preferable if such a method could be implemented with suitable operating equipment which would enable operating personnel to detect inflamed nerve roots quickly and easily, without satisfying lengthy training requirements.

SUMMARY OF THE INVENTION

Accordingly, it is an object of the present invention to provide a noninvasive method of ultrasonic detection of inflamed nerve roots. Therefore, a noninvasive method of ultrasonic detection of an inflamed nerve root adjacent to a spine of a patient is provided comprising the steps of: providing an ultrasound apparatus including an ultrasonic transducer interconnected with a source of electrical energy and a receiver preferably having amplification means; positioning the ultrasonic transducer on the patient's back in a location lateral to the spine; angling the ultrasonic transducer such that ultrasonic waves can be directed medialad to the spine; transmitting ultrasonic energy toward the nerve root at a power level and a frequency effective to create a reflection from an inflamed nerve root that is detectable by the ultrasound apparatus, wherein the ultrasonic energy transmitted toward the nerve root is directed medialad to the spine from a position lateral to the spine; and processing ultrasonic energy reflected from the nerve root with the ultrasound apparatus such that inflammation of the nerve root can be detected.

It is a further object of the present invention to provide suitable ultrasound equipment which enables health care professionals to use the present noninvasive method of ultrasonic detection of inflamed nerve roots in a manner that can be easily implemented such that operating personnel can detect inflamed nerve roots quickly and easily, without first satisfying lengthy training requirements.

While ultrasonic imaging is useful in many areas, prior to the present invention, it was believed that this technique was unsuitable for imaging nerve roots adjacent to the spine. It is believed that this has been primarily because the nerve roots are partially obscured by the bony material of the spinal process, which is generally believed to reflect ultrasound waves, and surrounded by ligamentous material or neurilemna, which is generally believed to absorb ultrasound waves. It is also believed that periosteum or ligamentous material surrounding the bone and areas adjacent to the bone can absorb ultrasound waves, thereby further complicating the potential for obtaining a clear image of any structural features of the anatomy adjacent to or in close proximity to the spine.

The success of the present inventive method indicates that the belief that ultrasound imaging of nerve roots will be prevented by the ligamentous material surrounding the nerve root is a belief which has misled those of skill in the art into incorrectly believing that ultrasound imaging is ineffective for imaging nerve roots which are inflamed. The present inventor, however, through years of experimentation using an early model B scanner, has learned that the ligamentous material or neurilemna surrounding the nerve roots does not prevent imaging of the nerve roots when they are inflamed. In fact, it is the belief of the present inventor that it is possible to ultrasonically detect a nerve root when, and, for the most part, only when, the nerve root is inflamed. This is very fortuitous, however, because this means that by detecting the nerve root, one can conclude that it is inflamed.

In order to scan the nerve roots to detect inflamed nerve roots, it is preferable to direct ultrasonic energy medialad to the spine from a transducer positioned in a location lateral to the spine on the back of a patient, preferably lying in a prone position. Although not herein relied upon, it is believed that it is only possible to detect nerve roots when the nerve roots are inflamed, and that this is because the nerve roots become swollen as they become inflamed. As they become swollen, it is believed that the ligamentous material surrounding the nerve roots is stretched in response to the swelling. Under this theory, when the ligamentous material is stretched, an ultrasonic image of the nerve roots can be obtained because the ligamentous material surrounding any particular nerve root is less capable of absorbing ultrasound wave energy in such a way so as to obscure the nerve root because of its reduced thickness in response to the stretching. It is believed that the greater the inflammation of the individual nerve root, the greater the intensity of the reflection which can be obtained from the nerve root. Under the present inventor's theory, this is because greater swelling is associated with greater inflammation, and greater swelling results in greater stretching. This, in turn, is believed to result in a tighter, more narrowly drawn condition in the tissues blanketing the nerve root area, concurrently raising the physical tone of the tissues which surround or encase the nerve root as well as, possibly, raising the physical tone of the nerve fibers which make up the nerve root. Although not relied upon, it is believed that these more or less simultaneous changes in tissue condition allow greater penetration of the blanket tissues by ultrasound waves, while causing greater reflection from the nerve fibers making up the nerve root or the tissue encasing the nerve root. Although not relied upon, it could be that the ligamentous surface coating or sheath surrounding the nerve root is simply more narrowly drawn and therefore more susceptible to penetration by ultrasound wave energy. If this is the case, the greater the penetration allowed, the greater, and perhaps more intense, the reflection from the underlying nerve root which is being scanned. It will be understood, however, that the applicant does not rely upon the theoretical presentations made herein, but rather presents them only for the purpose of discussing possible reasons for his findings respecting the usefulness of his present invention.

It will be appreciated that, without the present inventor's discovery, that inflamed nerve roots could indeed be detected using ultrasonic imaging techniques, those of skill in the art would continue to believe that such detection is ineffective, if not impossible. Therefore, without the present inventor's discovery respecting detection of inflamed nerve roots, there would have been no motivation to develop a noninvasive method of detecting inflammation of nerve roots using ultrasound imaging techniques.

As used in the present application, the following terms have the following meanings. A "nerve root" is a portion of the nervous system emerging from the spinal cord and/or exiting from the spinal canal lying just within or adjacent to the spinal column per se. It includes the nerve fibers proper (of which there may be hundreds or thousands, etc.) and/or their insulating coverings individually, the myelin sheathings, and/or the general coverings, the neurilemna, of the nerve trunk (defined further as multiple fibers grouped by and/or wrapped in neurilemna) and any other closely associated tissue which follow the course of the nerve root as it branches away from the cord and/or exits the spinal canal and/or lies just adjacent to the spine. An "ultrasonic transducer" is a device for converting electrical energy into ultrasonic or sound energy and for converting ultrasonic or sound energy into electrical energy. A "location lateral to the spine" is a location which is to one side of the length of the spine, or lateral to the length of the spine. The phrase "directed medialad to the spine" means directed toward the patient's spine from a position on the patient's back lateral to the length of the spine. And finally, "prone position" means a position wherein the spine is not flexed to a significant degree and the back of the patient faces generally toward the transducer, preferably the emitting surface of the transducer.

These and various other advantages and features of novelty which characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

BRIEF DESCRIPTION OF THE DRAWINGS

In the drawings, in which like reference numerals indicate corresponding parts of the preferred embodiments of the present invention throughout the several views.

DETAILED DESCRIPTION OF THE PREFERRED EMBODIMENTS

Figure 1:
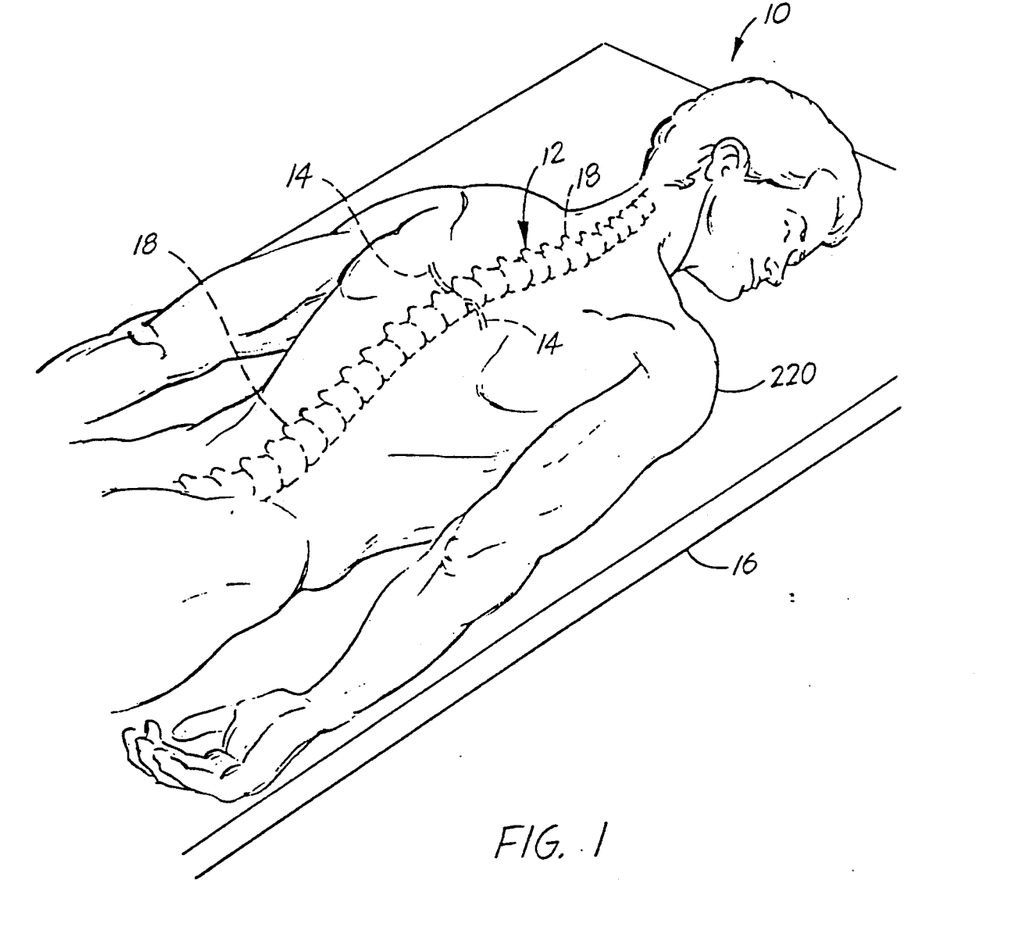
FIG. 1 shows a patient in a preferred position for an ultrasonic spine scan.
Figures 2A, 2B, 2C:
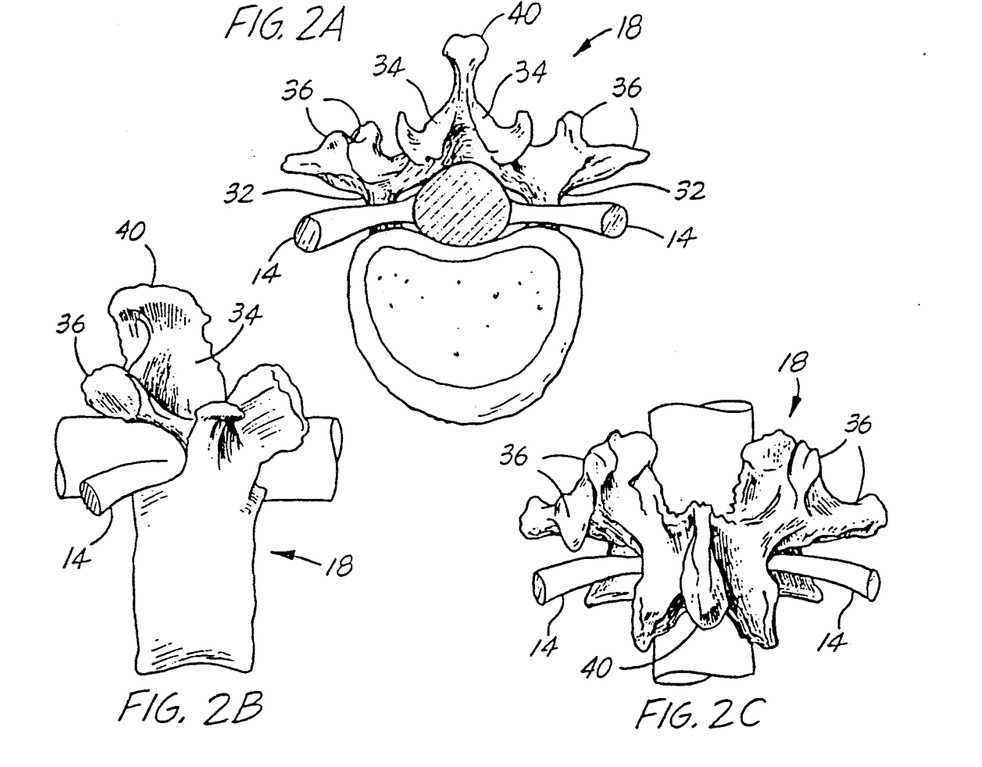
FIG. 2A shows is an inferior aspect view of a vertebra of the patient shown in FIG. 1, including an adjacent nerve root.
FIG. 2B shows is a lateral aspect of a vertebra of the patient shown in FIG. 1, including an adjacent nerve root.
FIG. 2C shows is a posterior aspect view of a vertebra including an adjacent nerve and several transducer head positions.

Referring now to the drawings, particularly FIG. 1 which shows a patient 10 having a spine 12 and nerve roots 14 lying on a support 16 in a substantially prone or flat position. It has previously been believed that detecting inflammation of nerve root 14 using ultrasonic energy was not possible because of the bony structure of vertebras 18 which make up spine 12. As shown in FIG. 2A, 2B, and 2C, each vertebra 18 includes two pedicles 32, two laminae 34, four articular processes 36, two transverse processes 38, and a spinous process 40, which in conjunction with or separately from the periosteum (not shown, but periosteum covers the surface of the bone) absorb and/or reflect ultrasonic energy, and thereby shield nerve roots 14 from such energy. Also, a sound absorbing and/or reflecting series of ligaments blankets the nerve roots 14 and can prevent sound waves from interacting with the nerve roots effectively even if the sound waves avoid the structural and geometric shield effects caused by the vertebral body and/or its periosteum.

Nevertheless, the present inventor has shown that it is possible to detect nerve roots 14 when they are inflamed. The more inflamed the nerve root, the easier it is to detect. However, if the nerve root 14 is not inflamed, it is not believed possible to detect it using known methods of ultrasonography. Although not relied upon, the ability to detect an inflamed nerve root 14 is believed possible only because of the swelling of the nerve root 14 which generally accompanies inflammation. The swelling is believed to stretch the ligamentous material surrounding the nerve root 14 such that ultrasonic energy is able to penetrate this covering without being excessively absorbed and so that ultrasound echoes or reflections from the nerve root 14 and/or neurilemna (not shown but closely wraps the nerve fibers forming an external sheathing effect) can be detected.

As shown in FIG. 1, the patient 10 should preferably be lying substantially flat, or in a non-flexed position. experimentation with other positions has revealed that a non-flexed patient position is preferred over other positions; indeed, other body postures may impede or make impossible detection of inflamed nerve roots 14.

Figure 3A:
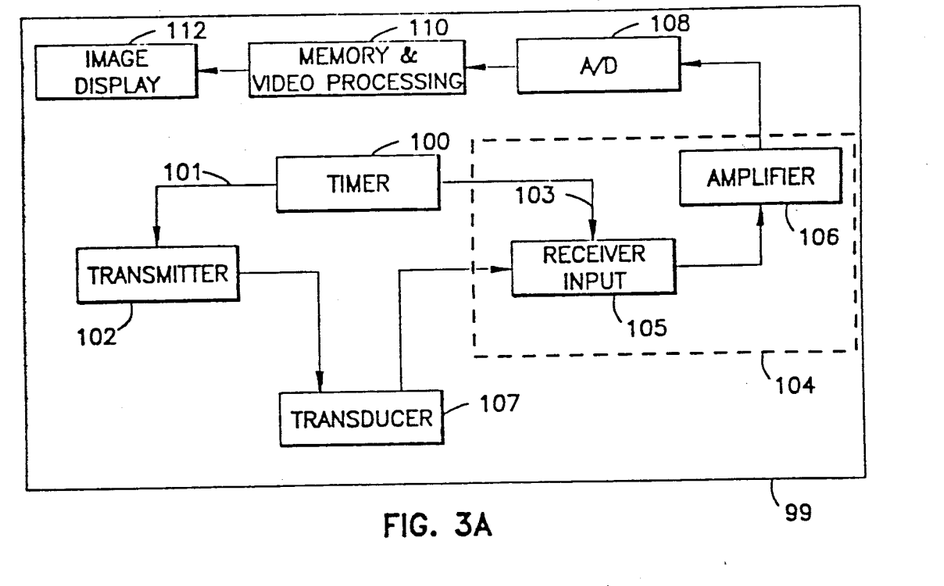
FIG. 3A is a functional block diagram of a preferred ultrasonic apparatus suitable for detecting an inflamed nerve root using the principles of the present invention.

An ultrasound apparatus 99 suitable for detecting an inflamed nerve root 14 according to the principles of the present invention is shown in FIG. 3A. Timer 100 is connected via line 101 to transmitter 102 and via line 103 to receiver input 105 of receiver 104. Timer 100 provides for various timekeeping functions within the ultrasound apparatus 99. A signal on line 101 keys transmitter 102 to transmit electrical energy into transducer 107. A signal on line 103 disables receiver 104 during the time transducer 107 generates ultrasonic energy.

Transmitter 102 injects electrical energy into transducer 107 with the characteristics necessary to cause transducer 107 to convert the electrical energy from transmitter 102 into ultrasonic energy. If transducer 107 is in contact with the patient 10, ultrasonic wave energy is then transmitted transcutaneously into the patient's body. The duration of the electrical energy from transmitter 102 is typically very narrow, which allows the transducer 107 to generate ultrasonic energy in short bursts and then listen for reflections from the inflamed nerve root 14 or spine 12 returning to the transducer 107.

Upon receiving reflections of ultrasonic energy, transducer 107 converts the reflected ultrasonic energy into an electrical signal which it sends to receiver 104. Receiver 104 has a receiver input 105 which receives the electrical signal from transducer 107, filters it to remove unwanted noise, and amplifies it by a fixed amount. The output from receiver input 105 is sent to amplifier 106. Amplifier 106 amplifies the signal from receiver input 105 by an amount determined by an external gain control adjustment available to operating personnel. Amplifier 106 sends the received and amplified signal resulting from the reflections detected by transducer 107 to A/D converter 108.

A/D converter 108 is an analog-to-digital converter which converts the analog signal from amplifier 106 to a digital signal which is generally a better form for processing. A/D converter 108 outputs its digital signal to memory and video processing network 110. Memory and video processing network 110 memorizes the representation of the reflection and processes it to be in a proper form for display on a video display screen. The output of memory and video processing network 110 is sent to image display 112 which graphically displays an image of the patient's internal structure on a screen (not shown) so that operating personnel can adjust the ultrasound apparatus 99 and position the transducer 107 to assist detection of the inflamed nerve root 14 and, upon detecting the inflamed nerve root 14, give the operating personnel a representation or an image of the inflamed nerve root 14 so that a diagnoses can be made.

Figure 3B:
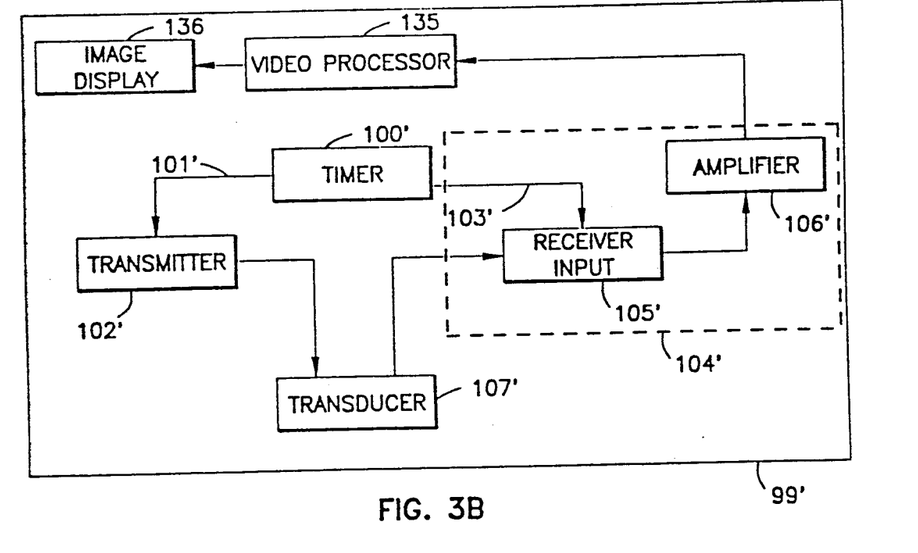
FIG. 3B is a functional block diagram of a low cost ultrasonic apparatus suitable for detecting an inflamed nerve root using the principles of the present invention.

An alternate embodiment of an ultrasonic apparatus suitable for detecting an inflamed nerve root 14 is shown in FIG. 3B. The apparatus of 3B is identical to that shown in FIG. 3A up to and including amplifier 106. However, instead of going to A/D converter 108, the signal from amplifier 106 goes to video processor 135. Video processor 135 analogically processes the signal from amplifier 106 and sends it in analog form to image display 136. The apparatus shown in FIG. 3B does not have the capability of FIG. 3A but typically results in a low cost apparatus.

According to the principles of the present invention transducer 107 must be located lateral to spine 12 and oriented with the correct angulation so that the ultrasonic energy can be directed medialad to the spine 12 and the respective nerve root 14 so that an inflamed nerve root 14 can be detected. It is to be understood that it is the beam angle, or the angle of transmission of the ultrasound waves, which matters and not the actual physical angle of the transducer 107 per se. However, it will be appreciated that by angling the transducer 107 the beam angle will be affected. This is important since some transducers 107 generate narrow beams of ultrasonic energy while others generate wide beams.

Figure 4:
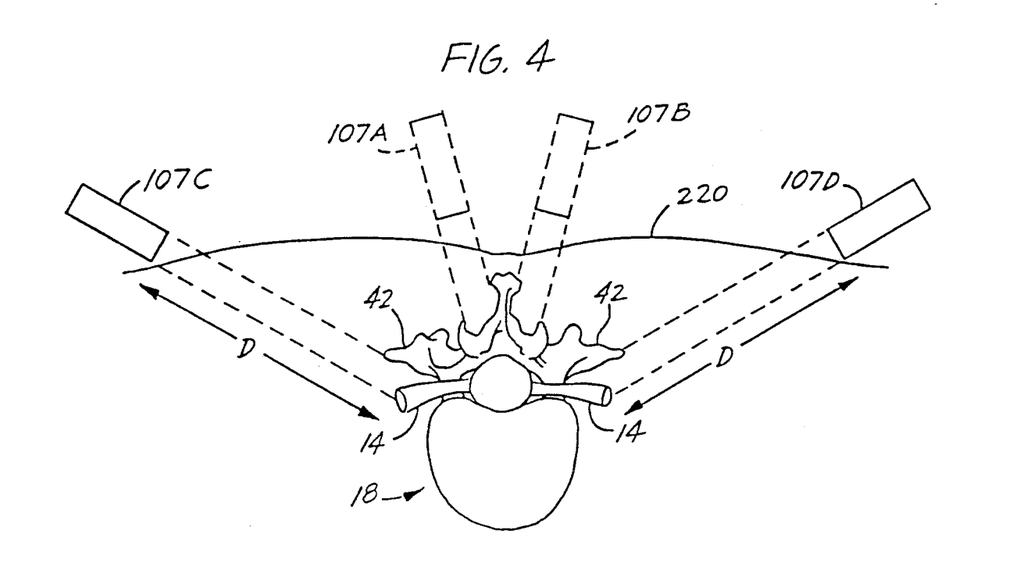
FIG. 4 illustrates the limitations on positioning of the transducer to detect an inflamed nerve root.

Referring now also to FIG. 4, a preferred angular position which enables sound waves to peer below the facet spread 42 of the respective vertebra 18 is illustrated. The best angle depends a great deal on the patient's body type. A steeper angle is preferred with large, heavy patients and a shallower angle is preferred with thin patients. If the angle is too steep, as shown in position 107A and 107B, the facet spread 42 can partially obscure the nerve root 14. If the angle is too shallow, as shown in position 107C and 107D, the distance that the ultrasonic wave travels through the body can cause excessive sound attenuation, which reduces the clarity of the image which can be obtained.

As mentioned above, one limitation on angulation is the attenuation of sound waves as they pass through the body. Attenuation is known to be frequency dependent, see for example Havlice and Taenzer ("Medical Ultrasonic Imaging: An Overview of Principles and Instrumentation", *Proceedings of the IEEE*, vol. 67 (4) pp.620-641). Sound waves at lower frequencies travel through body tissue more readily than sound waves having higher frequencies. Conversely, the use of higher frequencies improves system resolution. These factors, plus experimentation by the inventor, support the conclusion that a frequency of at least about 4.0 MHz, preferably 5 MHz, is believed to give the best performance. Preferably the operation frequency will be between about 4.0-7.5 MHz, more preferably between about 4.5-6.0 MHz.

Figure 5:
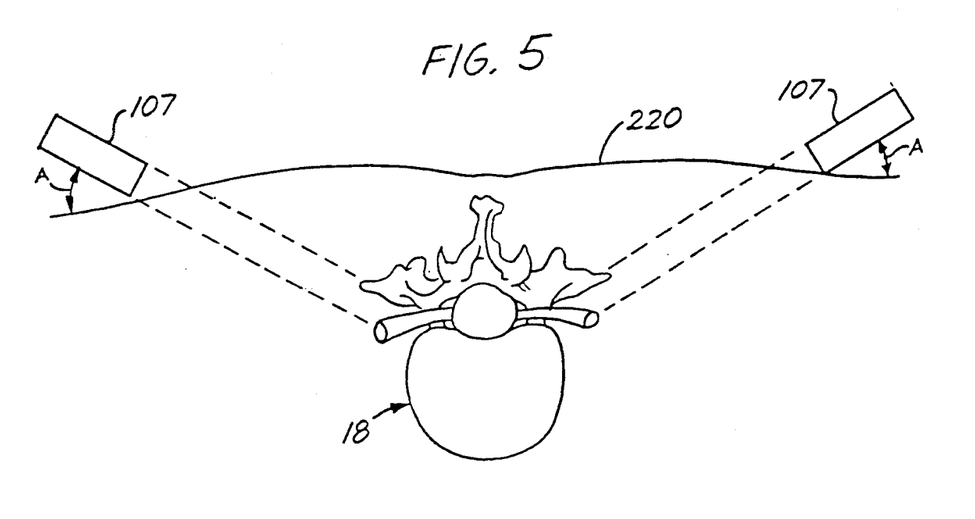
FIG. 5 illustrates the correct positioning of transducers to detect an inflamed nerve root.

With the understanding of the constraints on angulation, the correct angulation can be seen as critical. Referring now also to FIG. 5, a preferred angulation of the transducer 107 is illustrated. Experimentation has shown that a 60-degree beam angle relative to the skin 220, shown as angle A in FIG. 5, with the preferred operating frequency of 5 Mhz as described above, gives the best overall performance. However, the best angle will vary from patient to patient over a range of about 15 to 80 degrees.

While theoretically the correct frequency, operating angle, and transducer power output are sufficient to detect an inflamed nerve root 14, the process is simplified if the nerve root location is known prior to scanning the nerve root location adjacent to the spine. Healthy nerve roots are either not visible or barely visible using the ultrasonic techniques of the present invention, but inflamed nerves show up readily. Therefore, if a nerve root 14 is detected, it is presumed to be inflamed. The greater the reflection, the greater the inflammation is presumed to be. Since nerve root locations are well known with respect to anatomical structures of the spine 12, it is beneficial to scan the spine 12 to establish spinal landmarks; and then search for the nerve root 14 using these landmarks as reference points. This may be referred to as "vector windowing." The apparatus described above and shown in FIG. 3A is capable of performing rudimentary vector windowing when used by skilled operators.

Figure 6:
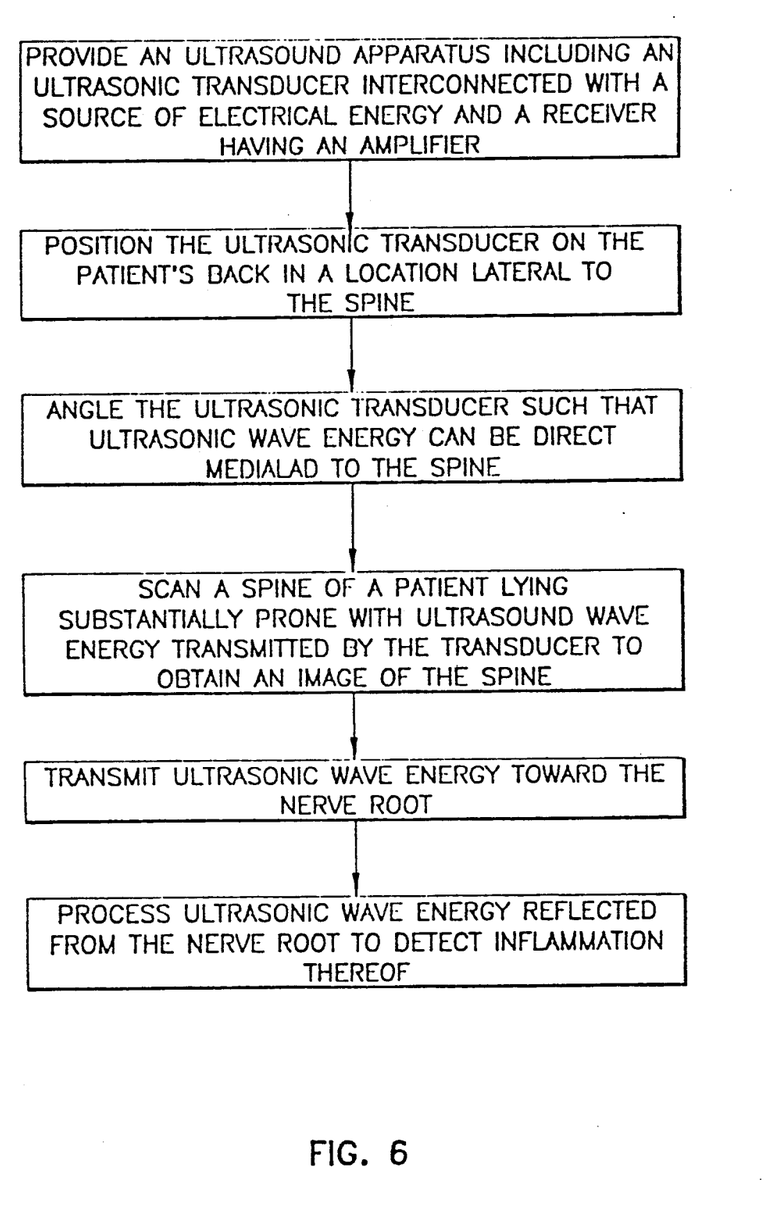
FIG. 6 is a flow chart of steps in a preferred method of detecting an inflamed nerve root according to the principles of the present invention.

The basic steps of the preferred method of ultrasonic detection of inflamed nerve roots 14 are shown in FIG. 6. An operator must provide a suitable ultrasound apparatus 99 including an ultrasonic transducer 107 interconnected with a source of electrical energy, transmitter 102, and with a receiver 104 having an amplifier 106, such as shown in FIG. 3A. Then the operator positions the ultrasonic transducer 107 on the patient's back in a location lateral to the spine. Next, the operator must angle the ultrasonic transducer 107 so that ultrasonic energy is directed medialad to the spine (see FIG. 5). Subsequently, the operator scans the patient's spine with ultrasonic energy when the patient is in a prone position to obtain an image of the spine. Following that, the operator causes ultrasonic energy to be transmitted toward the nerve root at a power level and a frequency effective to create a reflection from an inflamed nerve root 14 detectable by the ultrasound apparatus 99. The operator uses the image of the spine obtained in the previous step to obtain landmarks which are used to locate the nerve root position. Finally, the ultrasonic energy reflected from the nerve root is processed with the ultrasound apparatus 99 so that an image of the nerve root can be displayed and inflammation of the nerve root 14 can be detected.

The biggest problem with detecting an inflamed nerve root with the method described above is that the spine 12 must be scanned in such a manner that ultrasonic reflections from the spine 12 do not prohibit detection of the nerve root 14. This is important since reflections from the spine 12 are strong enough that objects close to it tend to be masked by the reflections from the spine, a condition referred to as a "washout".

There are several ways to avoid washout. One preferred method uses a "B" mode scanner having the capability of compound memorization of the reflections or images on a video screen. Compound means to add reflections or images together over several time periods to increase detection detail or the intensity of the visual representation of the nerve root 14. Repeatedly scanning the nerve root in compound mode then sums together nerve root echoes to permit visualization of the nerve root 14 despite the much stronger echo received from the bony material of the spine 12. Depending on the degree of inflammation, the frequency of the ultrasonic waves, and/or the amplification of the transduced echo by the receiver 104, any number of scans or transmitting events, wherein ultrasound waves are transmitted to the nerve root, can be required or preferred. Experimentation has shown that 2 to 6 scans are preferable at a frequency of 5.0 MHz. Preferably, a preferred apparatus (not shown) suitable for compounding images or echoes in this way would be similar to the apparatus 99 is illustrated in FIG. 3A except that the memory and video processing network 110 would have the additional capability of memorizing not only the present reflection but also several of the prior ones, and could compound them together and process the compounded reflections for display. The output of the memory and video processing network 110 sent to image display 112 would preferably contain information spanning a plurality of reflections or echoes. Examples of potential processing of compounded reflections include limiting the detection of strong reflections, illuminating or coloring weak reflections while dimming or differentially coloring strong ones, or only compounding reflections below a certain threshold, or only compounding reflections from certain areas per operator discretion.

Figure 7:
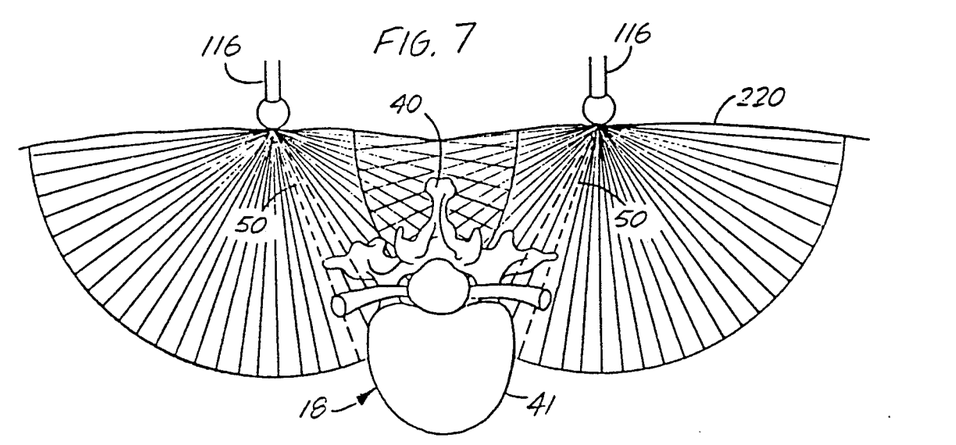
FIG. 7 illustrates a method of using sectoring transducers in accordance with the present invention to detect an inflamed nerve root.
Figure 8:
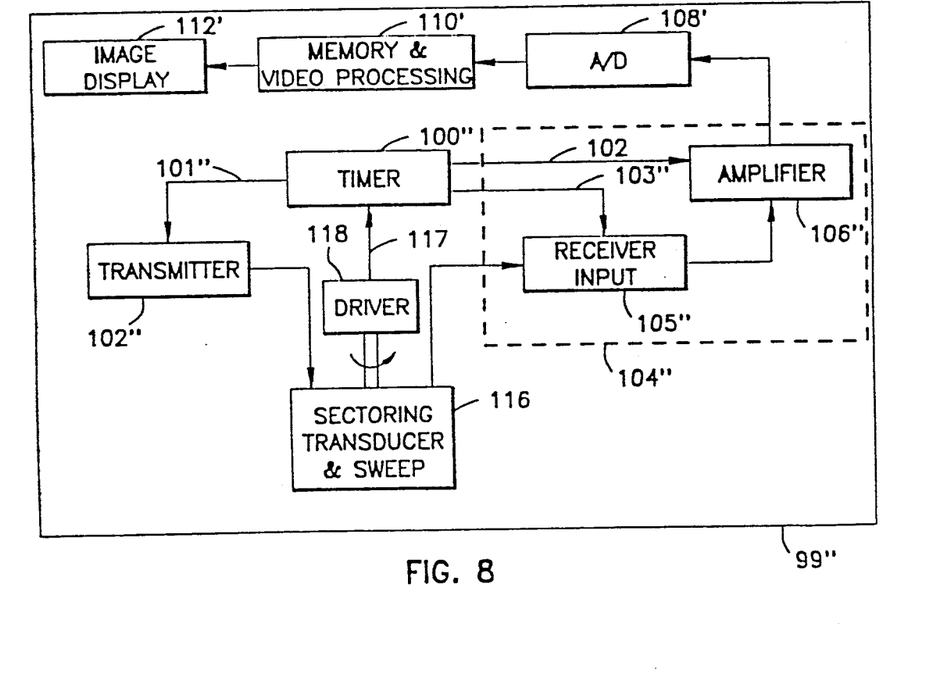
FIG. 8 is a functional block diagram of an ultrasonic apparatus suitable for detecting an inflamed nerve root using sectoring transducers.

Following the initial studies using a compounding "B" mode scanner, other preferred methods using other techniques have been developed. While not necessarily a part of the basic method, using two transducers allows both sides of spine to be scanned for inflamed nerve roots at the same time. Therefore, all figures from FIG. 7 onward that depict methods of detecting nerve root inflammation will show transducers on both sides of the spine. Shown in FIG. 7 is the preferred method of avoiding washout using sectoring transducers 116. A sectoring transducer generally remains in a fixed location that it rotates about, causing ultrasonic energy transmitted by the transducer to sweep across an area. In FIG. 7, each sectoring transducer 116 rotates through 180 degrees. An apparatus suitable for using a sectoring transducer to avoid washout is illustrated in FIG. 8. The apparatus of FIG. 8 operates identically as the apparatus of FIG. 3A, described above, except as noted below.

Referring to FIGS. 7 and 8, the power output of sectoring transducer 116 and the gain of amplifier 106" are adjusted so that a clean, clear outline of the vertebra 18 is displayed on image display 112' as sectoring transducer 116 rotates about its fixed position and ultrasonically sweeps vertebra 18. Using vertebra landmarks, such as the spinous process 40 and the vertebral body 41, a particular sweep angle 50 centered at angle 51, is scanned at a higher gain (or a higher transducer power output) in order to detect the nerve root 14 without washout. This method is termed sector windowing.

To implement the sector windowing method the apparatus of FIG. 8 contains a driver 118 which mechanically rotates sectoring transducer 116. The angular position of sectoring transducer 116 is sent to timer 100" by driver 118 on line 117. Additionally, timer 100" connects to amplifier 106" via line 127. When the angular position of sectoring transducer 116 is proper to cause the ultrasonic energy to be at sweep angle 50, timer 100" sends a signal to amplifier 106" which causes amplifier 106" to increase the amplification of the reflections until the ultrasonic energy leaves sweep angle 50. While this is the method of sector windowing in the preferred embodiment, another suitable method would be to increase the power of the ultrasonic energy from sectoring transducer 116 when the ultrasonic energy travels in sweep angle 50. Additionally, it is possible for the sectoring transducer to sweep the ultrasonic energy electronically without mechanical motion.

Figure 9:
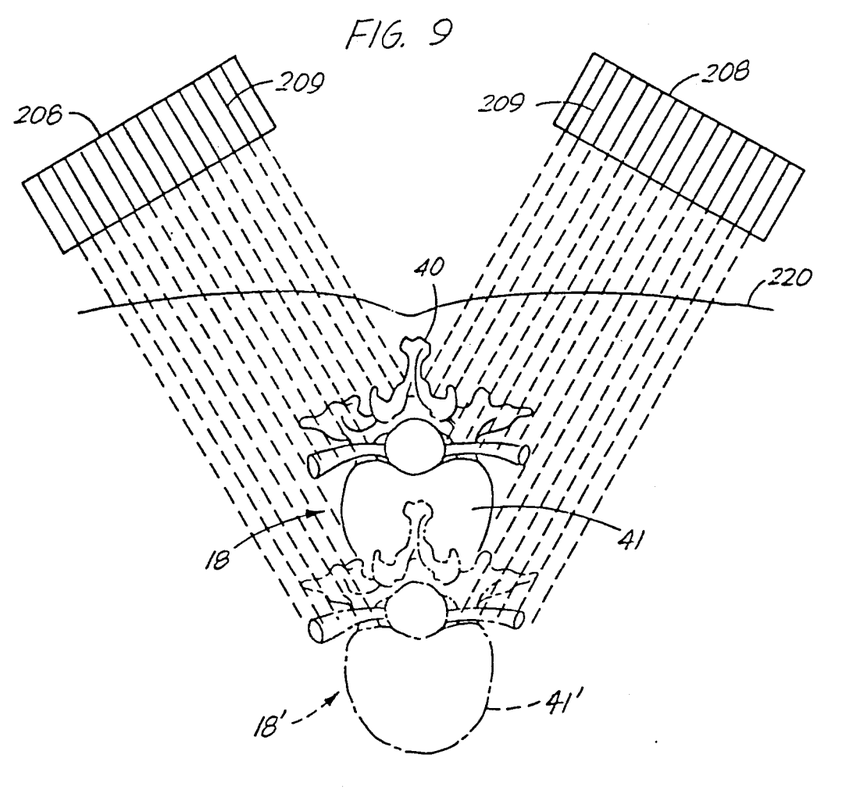
FIG. 9 illustrates a method of using a linear transducer array in accord with the present invention to detect an inflamed nerve root.

Another method of avoiding washout is shown in FIG. 9, where a linear transducer array 208, comprised of a large number of transducer elements 209, is placed on the skin 220 and directed toward the vertebra. Each transducer element 209 sequentially transmits ultrasonic energy into the body. Because each transducer element 209 is directed toward a particular area (some below and some at the vertebra 18), a summation of each transducer wavefront covers the vertebra 18. The output power of each transducer element 209 and the amplification of its reflections is adjusted to give a clear outline of the vertebra. Using portions of the vertebra, such as the spinous process 40 or the vertebra body 41 as reference landmarks, the amplification of the reflections detected by only the transducer elements (or power output of the transducer elements) directing ultrasound toward the nerve root 14 are increased to detect the inflamed nerve root. This method is called linear windowing.

Figure 10:
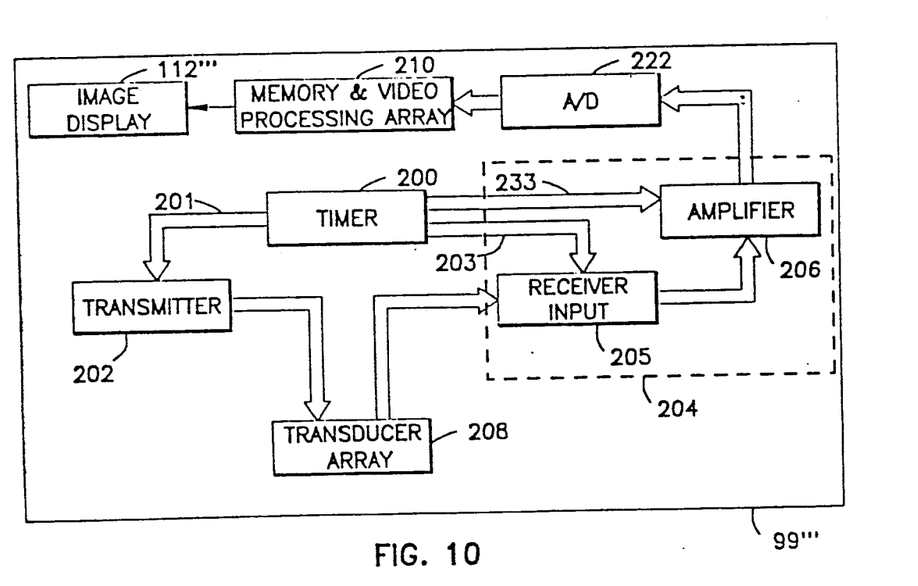
FIG. 10 is a functional block diagram of an ultrasonic apparatus suitable for detecting an inflamed nerve root using a linear transducer array.

An apparatus suitable for the above described method of linear windowing is illustrated in FIG. 10. Timer 200 connects to transmitter 202 via bus 201, to receiver array input 205 of receiver 204 via bus 203, and to amplifier array 206 of receiver 204 via bus 233. Timer 200 provides for various timekeeping and synchronization functions within the ultrasonic apparatus 99'''. Signals on bus 201 keys transmitter 202 to transmit electrical energy into linear transducer array 208. Signals on bus 203 disables receiver 204 during the time linear transducer array 208 generates ultrasonic energy.

Linear transducer array 208 contains transducer elements 209 as indicated above. Transmitter 202 injects electrical energy at a time directed by timer 200 into each transducer element 209 to cause each transducer element 209 to radiate ultrasonic energy. Reflections from the radiated ultrasonic energy are detected by transducer elements 209 and are sent to receiver 204 as electrical signals.

Receiver 204 has a receiver input 205 which receives the electrical signals from transducer elements 209, filters them to remove unwanted noise, and amplifies them by a fixed amount when enabled by timer 200 sending enabling signals on bus 203. The output from receiver input 205 is sent to amplifier array 206 which amplifies the signals by an amount determined by an external gain control adjustment available to operating personnel. The amplification is adjusted to give a clear outline of vertebra 18. Amplifier array 206 sends the received and amplified signal resulting from the reflections detected by linear transducer array 208 to A/D converter 222.

A/D converter 222 is an analog-to-digital converter which converts the analog signals from amplifier array 206 to digital signals which are a better form for processing. A/D converter 222 outputs its digital signals to memory and video processing network 210.

Memory and video processing network 210 memorizes the representations of the reflections and processes it to be in a proper form for display on a video display screen. The output of memory and video processing network 210 is sent to image display 112''' which graphically displays the patient's internal structure so that operating personnel can adjust the ultrasonic apparatus to assist detection of an inflamed nerve root 14.

Linear windowing is controlled by amplifier array 206 as a result of signals on bus 233 from timer 200.

After vertebra 18 is displayed on image display 112''', the operator would look for nerve root 14 by increasing the amplification of the reflections from the location of the nerve root. To accomplish this, signals on bus 233 cause amplifier array 206 to increase its amplification of reflections from those transducer elements 209 of transducer array 208 directed toward the location of nerve root 14.

Similarly, linear windowing can be accomplished by causing those transducer elements 209 of transducer array 208 directed toward the nerve root location to generate greater ultrasonic energy than those transducer elements 209 directed elsewhere. Control signals for increased power would then be applied via bus 201 to transmitter 202.

Figure 11:
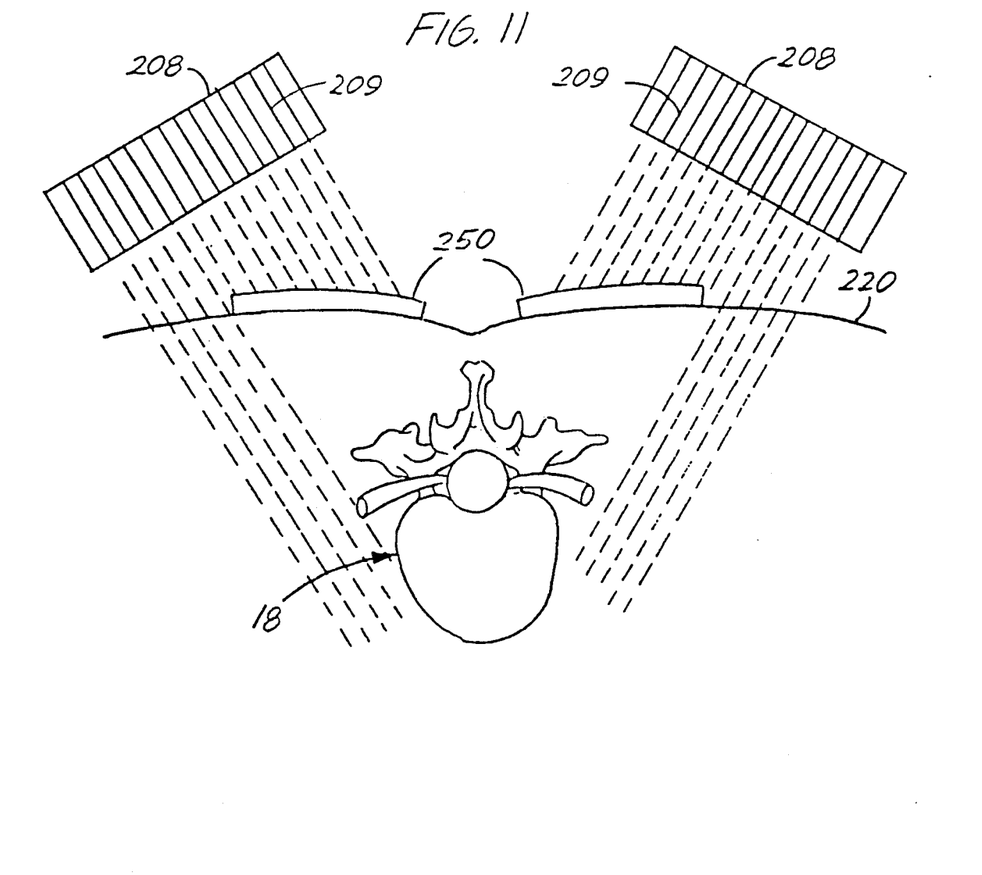
FIG. 11 illustrates a method of using an acoustic attenuator with a linear transducer array in accord with the present invention to moderate or eliminate reflections from vertebra.
Figure 12:
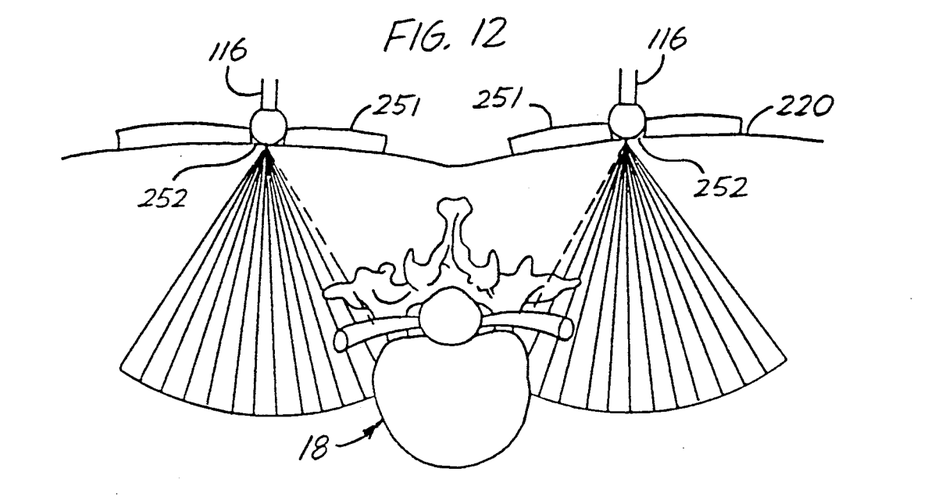
FIG. 12 illustrates a method of using an acoustic attenuator with sectoring transducers in accord with the present invention to moderate or eliminate reflections from vertebra.

It is possible to achieve the effects of sector windowing and linear windowing mechanically. This is accomplished by imposing an acoustic shield between the transducer and the patient to attenuate ultrasonic waves directed toward the spine. Shown in FIG. 11 is acoustic shield 250 disposed between linear transducer array 208 and the skin 220 of the patient. Acoustic shield 250 is positioned so that ultrasonic energy is hindered from striking vertebra 18. Since linear transducer 208 no longer receives strong ultrasonic energy reflections from vertebra 18, washout of the nerve root 14 is prevented. Similarly, FIG. 12 shows acoustic shield 251 having an opening 252 disposed between sectoring transducer 116 and the skin 22 of the patient. Acoustic shield 251 is positioned so that ultrasonic energy is hindered from striking vertebra 18 when sectoring transducer 116 rotates. Opening 252 can be adjusted to limit ultrasonic emissions and/or reflections to a narrow sweep angle. These methods are called mechanical windowing.

Another method of detecting an inflamed nerve root without washout is to use time variable gain (TVG). TVG can be use alone or with other washout prevention methods. TVG is based on the relationship between distance (D), speed (S), and time (T), $D = S \times T$. Since the speed of sound in tissue is relatively constant it is possible to find the distance of an object from the transducer by measuring the time it takes for sound from the transducer to reach it. Also, one can find a distance from a transducer by measuring the passage of time since transmission. In the TVG method, a nerve root is searched for by increasing the receiver amplification only where a nerve root should be. Additionally, the width of the time with increased gain could be adjusted to give a gain window.

Figure 13:
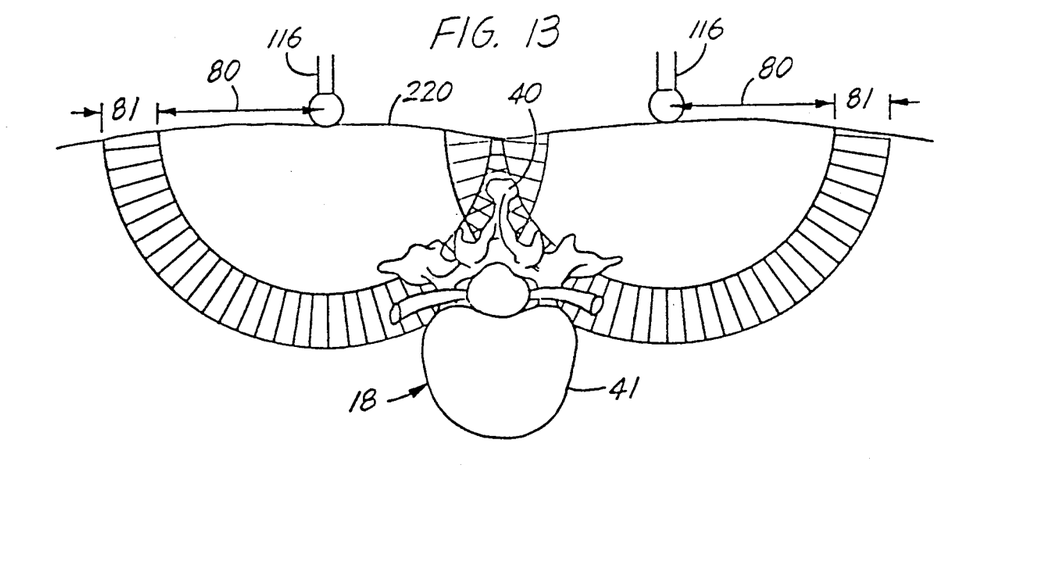
FIG. 13 illustrates time variable gain and its application to detecting inflamed nerve roots in accord with the present invention.

The method of using TVG to detect a nerve root is shown in FIG. 13. Sectoring transducer 116 sweeps ultrasonic energy as described above. However, the amplification of any reflections is kept very low until such time as the sound waves have traveled a distance 80. The receiver amplification gain is increased for a short period of time corresponding to the distance 81, and then reduced. Thus only objects at distances between 80 and (80+81) are detected. An apparatus suitable for doing this is illustrated in FIG. 8. The only modification would be that the signal from timer 100, on line 103 would enable the receiver 104 as a function of time rather than angular position. A similar method can be used with a linear transducer array. The choice of a sectoring transducer in the explanation was for clarity.

Since spinal nerve roots emanate from both sides of the spine it is convenient to perform the method of the present invention on both sides simultaneously, as mentioned above and as illustrated in FIGS. 7, 9, 11, 12, and 13. It is convenient to join together the transducers or transducer arrays with a handle to allow operating personnel to have a convenient method of positioning them.

Figure 14:
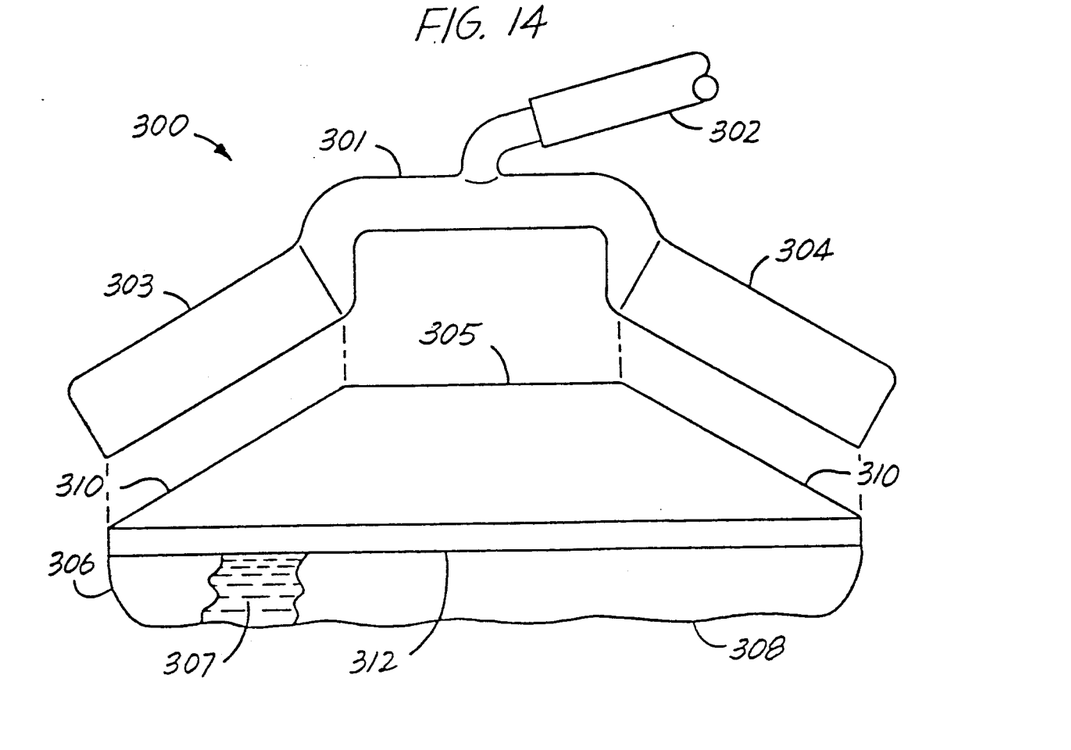
FIG. 14 shows a schematic representation of a preferred embodiment of a linear transducer assembly of the present invention including transducer arrays, handle, ultrasonic transmitting material and bag.

FIG. 14 shows a preferred embodiment of the construction of a linear transducer assembly 300. It includes a plastic handle 301 for gripping by operating personnel. Connected to the handle is cable 302 used for electronic communication between the transducer arrays (not shown) in linear heads 303 and 304 and operating electronics. Rigidly attached to handle 301 on a first side is a first linear head 303 and on a second side is a second linear head 304. Handle 301 maintains the spacing between linear heads 303 and 304 at approximately 5.5 cm, measured from the nearest points on each linear head. Also, handle 301 maintains each linear head at an appropriate angle relative to the skin surface with respect to the axis of the handle as discussed previously. Each linear head is of approximately equal length and dimensioned so that the distance between the furthest apart edges of linear heads 303 and 304 is about 13 cm. Linear heads 303 and 304 are made from plastic or other non conductive material and contain transducer elements equivalent to transducer elements 209 discussed above.

Additionally, linear transducer assembly 300 has a body 305 made from an ultrasonic conductive plastic above a filled bag 306 containing oil 307 or other suitable sound conducting media. Filled bag 306 has a flexible bottom surface 308. As shown in FIG. 14, body 305 is dimensioned to hold linear heads 303 and 304. When ultrasonic energy is generated in either linear head 303 or 304, the ultrasonic energy is coupled between the linear head and the body 305 at interface 310. The energy travels through body 305 and is coupled into the filled bag at interface 312. The energy travels through oil 307, or other suitable sound conducting media, to flexible surface 308. Flexible surface 308 will form an interface with a patients back via a thin film of oil or other suitable material during scanning. As shown if FIG. 14, in the preferred embodiment the combination of linear heads 303 and 304, handle 301, and cable 302 are separable from the body 305. However, during scanning, linear heads 303 and 304, the handle 301 and the body 305 are mechanically and acoustically coupled together.

Figure 15:
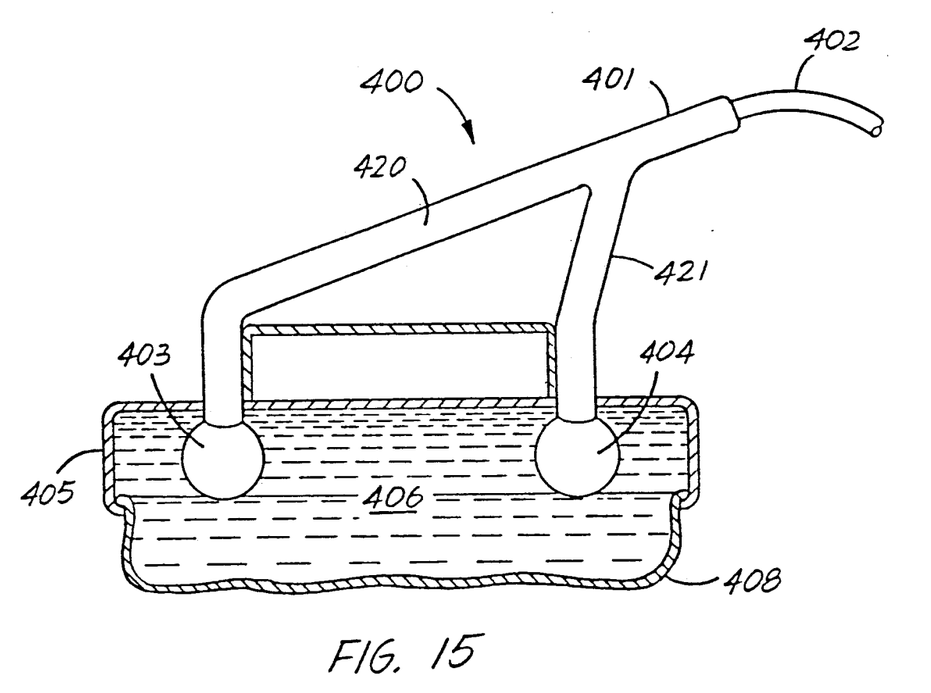
FIG. 15 shows a schematic representation of a preferred embodiment of a dual sectoring transducer assembly of the present invention including sectoring transducers, handle, body, and filled bag.

FIG. 15 show a preferred embodiment of the construction of a sectoring transducer assembly 400. It includes a plastic handle 401 for gripping by operating personnel. Connected to the handle is cable 402 used for electronic communication between the transducers 403 and 404 and operating electronics. Handle 401 splits into a first frame member 420 and a second frame member 421. Rigidly attached to frame member 420 is a first sectoring transducer 403. Similarly, rigidly attached to frame member 421 is a second sectoring transducer 404. Handle 401 maintains the spacing between sectoring transducers 403 and 404 at approximately 6.5 cm, measured from center to center. The body of sectoring transducers 403 and 404 are made from plastic and contain transducers equivalent to sectoring transducer 116 discussed above.

Additionally, sectoring transducer assembly 400 has a body 405 containing oil 406, or other suitable sound conducting media. Body 405 includes a soft bladder which forms a flexible surface 408. As shown in FIG. 15, body 405 is dimensioned to hold sectoring transducers 403 and 404. When ultrasonic energy is generated in either sectoring transducer 403 or 404, the ultrasonic energy is coupled between the sectoring transducers and the body 405. The energy travels through body 405 and to flexible surface 408. Flexible surface 408 will form an interface via a thin film of oil or other suitable material spread on the patient's back during scanning.

If both sides of the spine are scanned it would be useful to have a video display unit capable of displaying the spine in various ways. Merging the images from both transducers together would be useful as would be the ability of rotating the image as required. Additionally, it would be useful to have the image digitized so that images of the same nerve over time could be compared or nerve roots from different people could be analyzed.

To assist in understanding the principles of the present invention, a step-by-step method of detecting an inflamed nerve root will be given. First a suitable apparatus must be obtained. For example a ultrasound "B" mode apparatus which includes an ultrasonic transducer interconnected with a source of electrical energy and a receiver including an amplifier. Next the transducer must be positioned on the patient's back when the patient is lying in a prone position at a location lateral to the spine and angled such that ultrasonic energy can be directed medialad toward the spine. Next, the spine of a patient should be scanned to obtain a clear and distinct video image of the spine. Next, the nerve root location should be scanned, using landmarks from the spinal vertebra as references, without washing out from reflections from the spine. Using a "B" mode apparatus this would entail compounding, or adding, two to six echoes received from the vicinity of the nerve root locations. Finally, a determination of the condition of the nerve root should be made. If the nerve root is detectable, it is believed to be inflamed, with the strength of reflections from the nerve root being an indicator of the degree of nerve root inflammation.

It is to be understood, however, that even though numerous characteristics and advantages of the present invention have been set forth in the foregoing description, together with details of the structure and function of the invention, the disclosure is illustrative only, and changes may be made in detail within the principles of the invention to the full extent indicated by the broad general meaning of the terms in which the appended claims are expressed.

What is claimed is:

1. A method of detecting inflammation of a nerve root adjacent to a spine of a patient, said method comprising the steps of:
   (a) providing an ultrasound apparatus including an ultrasonic transducer interconnected with a source of electrical energy and with a receiver having amplification means;
   (b) positioning the ultrasonic transducer on the patient's back in a location lateral to the spine;
   (c) angling the ultrasonic transducer such that ultrasonic energy can be directed medialad to the spine;
   (d) transmitting ultrasonic energy from said ultrasonic transducer toward the nerve root at a power level and a frequency effective to create a reflection from an inflamed nerve root that is detectable by the ultrasound apparatus, wherein the ultrasonic energy transmitted from said ultrasonic transducer toward the nerve root is directed medialad to the spine from a position lateral to the spine; and
   (e) processing ultrasonic energy reflected from the nerve root to said ultrasonic transducer with the ultrasound apparatus such that inflammation of the nerve root can be detected.

2. The method of claim 1 wherein the step of positioning the ultrasonic transducer includes positioning the ultrasonic transducer when the patient is lying in a substantially prone position.

3. The method of claim 2, further including the step of scanning the spine of the patient with ultrasound energy transmitted by the transducer to obtain an image of the spine prior to processing the ultrasonic energy reflected from the nerve root, wherein the step of processing the ultrasonic energy reflected from the nerve root includes using the image of the spine obtained from said scanning step as a reference for locating an image of an inflamed nerve root.

4. The method of claim 3, wherein the step of processing ultrasonic energy reflected from the nerve root includes increasing the amplification of the receiver for ultrasonic energy reflected from the nerve root.

5. The method of claim 3, wherein the step of transmitting ultrasonic energy includes transmitting greater ultrasonic energy in the direction of the nerve root than elsewhere.

6. The method of claim 5, wherein the step of transmitting greater ultrasonic energy in the direction of the nerve root that elsewhere includes controlling the distribution of ultrasonic energy by an acoustical aperture in an acoustical attenuator.

7. A method of detecting inflammation of a nerve root adjacent to a spine of a patient, said method comprising the steps of:
   (a) providing an ultrasound apparatus including an ultrasonic transducer interconnected with a source of electrical energy and with a receiver having an amplification means;
   (b) scanning the spine of the patient with ultrasound energy transmitted by the transducer to obtain an image of the spine;
   (c) positioning the ultrasonic transducer on the patient's back in a location lateral to the spine;
   (d) angling the ultrasonic transducer such that ultrasonic energy can be directed medialad to the spine;
   (e) transmitting ultrasonic energy from said ultrasonic transducer toward the nerve root at a power level and a frequency effective to create a reflection from an inflamed nerve root that is detectable by the ultrasound apparatus, wherein the ultrasonic energy transmitted from said ultrasonic transducer toward the nerve root is directed medialad to the spine from a position lateral to the spine; and
   (f) processing ultrasonic energy reflected from the nerve root to said ultrasonic transducer with the ultrasound apparatus such that inflammation of the nerve root can be detected using the image of the spine obtained from said scanning step as a reference for locating an image of an inflamed nerve root.

8. The method of claim 7 wherein the step of positioning the ultrasonic transducer includes positioning the ultrasonic transducer when the patient is lying in a substantially prone position.

9. The method of claim 8, wherein the step of processing ultrasonic energy reflected from the nerve root includes increasing the amplification of the receiver for ultrasonic energy reflected from the nerve root.

10. The method of claim 8, wherein the step of transmitting ultrasonic energy includes transmitting greater ultrasonic energy in the direction of the nerve root than elsewhere.

11. The method of claim 10, wherein the step of transmitting greater ultrasonic energy in the direction of the nerve root than elsewhere includes controlling the distribution of ultrasonic energy by an acoustical aperture in an acoustical attenuator.

12. A method of detecting inflammation of a nerve root adjacent to a spine of a patient, said method comprising the steps of:
   (a) providing an ultrasound apparatus including an ultrasonic sectoring transducer interconnected with a source of electrical energy and with a receiver having an amplification means;
   (b) positioning the ultrasonic sectoring transducer on the patient's back in a location lateral to the spine;
   (c) angling the transducer such that ultrasonic energy from the ultrasonic sectoring transducer is directed medialad to the spine;
   (d) transmitting ultrasonic energy from said ultrasonic sectoring transducer toward the nerve root at a power level and a frequency effective to create a reflection from an inflamed nerve root that is detectable by the ultrasound apparatus, wherein the ultrasonic energy transmitted from said ultrasonic sectoring transducer toward the nerve root is directed medialad to the spine from a position lateral to the spine; and
   (e) processing ultrasonic energy reflected from the nerve root to said ultrasonic sectoring transducer with the ultrasound apparatus such that inflammation of the nerve root can be detected.

13. The method of claim 12, wherein the step of positioning the ultrasonic sectoring transducer includes positioning the ultrasonic sectoring transducer when the patient is lying in a substantially prone position.

14. The method of claim 13, further including the step of scanning the spine of the patient with ultrasound energy transmitted by the transducer to obtain an image of the spine prior to processing the ultrasonic energy reflected from the nerve root, wherein the step of processing the ultrasonic energy reflected from the nerve root includes using the image of the spine obtained from said scanning step as a reference for locating an image of an inflamed nerve root.

15. The method of claim 14, wherein the step of processing ultrasonic energy reflected from the nerve root with the ultrasound apparatus includes increasing the amplification of the receiver for ultrasonic energy reflected from the nerve root.

16. The method of claim 15, wherein the step of processing ultrasonic energy reflected from the nerve root with the ultrasound apparatus includes increasing the amplification of the receiver at a first time occurring after ultrasonic energy is transmitted and decreasing the amplification of the receiver at a second time occurring after the first time.

17. A sectoring ultrasonic apparatus suitable for noninvasive ultrasonic scanning of a patient's spinal nerve roots, said patient having a back, nerve roots, and a spine within the back, the back including first and second sides lateral to the length of the spine, the nerve roots being located adjacent to the spine, said sectoring ultrasonic apparatus comprising:
   means for generating an ultrasound signal;
   a first sectoring transducer electrically coupled to said generating means for contacting a first side of the patient's back and transmitting said ultrasound signal to the patient's spine;
   means electrically coupled to said first sectoring transducer for processing an ultrasonic signal reflected from said spinal nerve roots to said first sectoring transducer;
   a second sectoring transducer electrically coupled to said generating means and said processing means for contacting the second side of the patient's back and for transmitting said ultrasound signal to the patient's spine echoes; and
   handle means rigidly connected to both said first and second sectoring transducers, said handle means for keeping said first and second sectoring transducers in a substantially fixed, spaced apart relationship suitable for ultrasonically scanning nerve roots from both the first and second sides of the back without moving said handle means.

18. The apparatus of claim 17, wherein said handle means spaces said first and second sectoring transducers between 2 and 30 cm apart.

19. A method of ultrasonically detecting inflammation of a nerve root adjacent to a spine of a patient, said method comprising the steps of:
   (a) providing an ultrasound apparatus including an ultrasonic transducer having a linear array of elements interconnected with a source of electrical energy and with a receiver having an amplification means;
   (b) positioning the ultrasonic transducer on the patient's back in a location lateral to the spine;
   (c) angling the ultrasonic transducer such that ultrasonic energy from the linear array can be directed medialad to the spine;
   (d) transmitting ultrasonic energy from said ultrasonic transducer toward the nerve root at a power level and a frequency effective to create a reflection from an inflamed nerve root that is detectable by the ultrasound apparatus, wherein the ultrasonic energy transmitted from said ultrasonic transducer toward the nerve root is directed medialad the spine from a position lateral tot he spine; and
   (e) processing ultrasonic energy reflected from the nerve root to said ultrasonic transducer with the ultrasound apparatus such that inflammation of the nerve root can be detected.

20. The method of claim 19, wherein the step of positioning the ultrasonic transducer includes positioning the ultrasonic transducer when the patient is lying in a substantially prone position.

21. The method of claim 20, further including the step of scanning the spine of the patient with ultrasound energy transmitted by the transducer to obtain an image of the spine prior to processing the ultrasonic energy reflected from the nerve root, wherein the step of processing the ultrasonic energy reflected from the nerve root includes using the image of the spine obtained from said scanning step as a reference for locating an image of an inflamed nerve root.

22. The method of claim 21, wherein the step of processing ultrasonic energy reflected from the nerve root with the ultrasound apparatus includes increasing the amplification of the receiver in those ultrasonic transducer elements receiving reflections from the nerve root.

23. The method of claim 22, wherein the step of processing ultrasonic energy reflected from the nerve root with the ultrasound apparatus includes increasing the amplification of the receiver at a first time occurring after ultrasonic energy is transmitted and decreasing the amplification of the receiver at a second time occurring after the first time.

24. A device for ultrasound imaging including a linear transducer array having a plurality of elements, the transducer array being suitable for noninvasive ultrasonic scanning of a patient's spinal nerve roots, said patient having a back, nerve roots, and a spine within the back, the back including first and second sides lateral to the length of the spine, the nerve roots being located adjacent to the spine, said linear transducer array comprising:

means for generating an ultrasonic imaging signal;

a first transducer array electrically coupled to said generating means which can generate ultrasonic wave fronts from said ultrasonic imaging signal directed medialad toward patient's spine from a plurality of transducer elements and which can receive ultrasonic energy reflections, said ultrasonic wave fronts of sufficient dimension to image a vertebra;

a second transducer array electrically coupled to said generating means which can generate ultrasonic wave fronts from said ultrasonic imaging signal directed medialad toward patient's spine from a plurality of transducer elements and which can receive ultrasonic energy reflections, said ultrasonic wave fronts of sufficient dimension to image a vertebra;

handle means rigidly connected to both said first and second transducer arrays, said handle means for keeping said first and second transducer arrays in a substantially fixed, spaced apart relationship suitable for ultrasonically detecting an inflamed nerve root from both sides of the back without moving said handle means; and means electrically coupled to said first transducer array and said second transducer array for processing said ultrasonic energy reflections to display said inflamed nerve root.

25. The apparatus of claim 24, further including interface means for interfacing with the patient's back, said interface means being connected to said first and second transducer arrays wherein said ultrasonic energy passes through said interface means

* * * * *